United States Patent [19]

Brooks et al.

[11] Patent Number: 5,187,192

[45] Date of Patent: Feb. 16, 1993

[54] CYCLOBUTYL DERIVATIVES HAVING LIPOXYGENASE INHIBITORY ACTIVITY

[75] Inventors: Dee W. Brooks, Libertyville, Ill.; Karen E. Rodriques, Stowe, Mass.

[73] Assignee: Abbott Laboratories, Abbott Park, Ill.

[21] Appl. No.: 850,719

[22] Filed: Mar. 13, 1992

[51] Int. Cl.$^5$ .................. A61K 31/38; C07D 332/34; C07D 332/32

[52] U.S. Cl. ...................... 514/445; 514/63; 514/351; 514/357; 514/512; 514/575; 514/469; 514/470; 514/471; 514/438; 514/443; 514/336; 546/283; 546/284; 546/291; 546/332; 546/300; 549/51; 549/54; 549/55; 549/58; 549/65; 549/76; 549/77; 549/467; 549/493; 549/469; 549/479; 560/313; 562/621; 562/622; 562/623; 562/874; 556/436; 558/262; 552/35

[58] Field of Search ............... 549/479, 493, 467, 469; 549/65, 76, 77, 51, 54, 55, 58; 562/623, 622, 621, 874; 546/283, 284, 291, 332, 300; 514/351, 357, 375, 512, 63, 471, 469, 470, 438, 445, 336; 558/443; 556/262, 936

[56] References Cited

U.S. PATENT DOCUMENTS 4,738,986  4/1988  Keen et al. ........................ 562/621
4,988,733  1/1991  Salmon et al. .................... 562/621
5,120,752  6/1992  Brooks et al. .

FOREIGN PATENT DOCUMENTS

WO92/09567  6/1992  World Int. Prop. O. .

Primary Examiner—Carolyn Elmore
Assistant Examiner—Mark W. Russell
Attorney, Agent, or Firm—Dee W. Brooks; Karen E. Rodriques

[57] ABSTRACT

Compounds of the structure

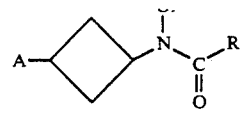

where M is a pharmaceutically acceptable cation or a metabolically cleavable group, R is alkyl, cycloalkyl or —$NR^1R^2$, where $R^1$ and $R^2$ are hydrogen, alkyl, cycloalkyl or alkanoyl, and A is optionally substituted alkyl, cycloalkyl, carbocyclic aryl, benzo[b]furyl, thienyl, or benzo[b]thienyl are potent inhibitors of lipoxygenase enzymes and thus inhibit the biosynthesis of leukotrienes. These compounds are useful in the treatment or amelioration of allergic and inflammatory disease states.

11 Claims, No Drawings

CYCLOBUTYL DERIVATIVES HAVING LIPOXYGENASE INHIBITORY ACTIVITY

TECHNICAL FIELD

This invention relates to compounds having biological activity to inhibit lipoxygenase enzymes, to pharmaceutical compositions comprising these compounds, and to a medical method of treatment. More particularly, this invention concerns certain substituted cyclobutyl ureas and hydroxamic acids which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 0 299 761 to Salmon, et al. discloses and claims certain (substituted phenoxy)-phenylalkenyl hydroxamic acids and their salts which are useful as agents for inhibiting lipoxygenase and cyclooxygenase activity.

SUMMARY OF THE INVENTION

In its principal embodiment, the present invention provides certain substituted cyclobutyl compounds which inhibit lipoxygenase enzyme activity and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The compounds of this invention have the structure

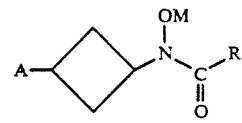

or a pharmaceutically acceptable salt thereof where the group M represents hydrogen, a pharmaceutically acceptable cation, or a pharmaceutically acceptable metabolically cleavable group.

The group R is selected from hydrogen, alkyl of from one to twelve carbon atoms, cycloalkyl of from three to eight carbon atoms, and $—NR^1R^2$. In the group $—NR^1R^2$, $R^1$ is selected from hydrogen, alkyl of from one to six carbon atoms, hydroxyalkyl of from one to six carbon atoms, and alkoxyalkyl in which the alkoxy portion and the alkyl portion each contain, independently, from one to six carbon atoms.

$R^2$ is selected from hydrogen, alkyl of from one to six carbon atoms, hydroxyalkyl of from one to six carbon atoms, alkoxyalkyl in which the alkoxy portion and the alkyl portion each contain, independently, from one to six carbon atoms, alkanoyl of from two to eight carbon atoms, alkyl(carbocyclic aryl) in which the alkyl portion contains from one to six carbon atoms, and carbocyclic aryl.

The group A is selected from (a) alkyl of from five to twenty carbon atoms; (b) cycloalkyl of from three to eight carbon atoms; (c) optionally substituted carbocyclic aryl; (d) optionally substituted (carbocyclic aryl)alkyl in which the alkyl portion may contain from one to six carbon atoms; (e) optionally substituted (carbocyclic aryl)cycloalkyl in which the cycloalkyl portion contains from three to eight carbon atoms; (f) optionally substituted carbocyclic aryloxyalkyl in which the alkyl portion contains from one to six carbon atoms; (g) optionally substituted (carbocyclic aryl)alkoxyalkyl in which the alkoxyl and alkyl portions may independently contain from one to six carbon atoms; and (h) optionally substituted carbocyclic arylthioalkyl in which the alkyl portion may contain from one to six carbon atoms.

In all of the foregoing, the optional substituents on the carbocyclic aryl groups are selected from the group consisting of (1) alkyl of from one to six carbon atoms; (2) haloalkyl of from one to six carbon atoms; (3) alkoxy of from one to twelve carbon atoms; (4) phenyl, optionally substituted with alkyl of from one to six carbon atoms, haloalkyl of from one to six carbon atoms, alkoxy of from one to six carbon atoms, and halogen; (5) phenoxy, optionally substituted with alkyl of from one to six carbon atoms, haloalkyl of from one to six carbon atoms, alkoxy of from one to six carbon atoms, and halogen; (6) phenylthio, optionally substituted with alkyl of from one to six carbon atoms, haloalkyl of from one to six carbon atoms, alkoxy of from one to six carbon atoms, and halogen; (7) 2-, 3-, or 4-pyridyl, optionally substituted with alkyl of from one to six carbon atoms, haloalkyl of from one to six carbon atoms, alkoxy of from one to six carbon atoms, and halogen; and (8) 2-, 3-, or 4-pyridyloxy, optionally substituted with alkyl of from one to six carbon atoms, haloalkyl of from one to six carbon atoms, alkoxy of from one to six carbon atoms, and halogen.

The group A may further represent a heterocyclic substituent selected from (i) 2- or 3-furyl, optionally substituted with (i1) alkyl of from one to six carbon atoms; (i2) haloalkyl of from one to six carbon atoms; (i3) alkoxy of from one to six carbon atoms; or (i4) halogen; (i5) phenyl, optionally substituted with (i5a) alkyl of from one to six carbon atoms, (i5b) haloalkyl of from one to six carbon atoms, (i5c) alkoxy of from one to six carbon atoms, or (i5d) halogen, (i6) phenoxy, optionally substituted with (i6a) alkyl of from one to six carbon atoms, (i6b) haloalkyl of from one to six carbon atoms, (i6c) alkoxy of from one to six carbon atoms, or (i6d) halogen; (i7) phenylthio, optionally substituted with (i7a) alkyl of from one to six carbon atoms, (i7b) haloalkyl of from one to six carbon atoms, (i7c) alkoxy of from one to six carbon atoms, or (i7d) halogen, (i8) 2-, 3-, or 4-pyridyl, optionally substituted with (i8a) alkyl of from one to six carbon atoms, (i8b) haloalkyl of from one to six carbon atoms, (i8c) alkoxy of from one to six carbon atoms, or (i8d) halogen, (i9) 2-, 3-, or 4-pyridyloxy, optionally substituted with (i9a) alkyl of from one to six carbon atoms, (i9b) haloalkyl of from one to six carbon atoms, (i9c) alkoxy of from one to six carbon atoms, or (i9d) halogen, (j) benzo[b]furyl, optionally substituted with (j1) alkyl of from one to six carbon atoms, (j2) haloalkyl of from one to six carbon atoms, (j3) alkoxyl of from one to six carbon atoms, and (j4) halogen; (k) 2- or 3-thienyl, optionally substituted with (k1) alkyl of from one to six carbon atoms; (k2) haloalkyl of from one to six carbon atoms; (k3) alkoxy of from one to six carbon atoms; (k4) halogen; (k5) phenyl, optionally substituted with (k5a) alkyl of from one to six carbon atoms, (k5b) haloalkyl of from one to six carbon atoms, (k5c) alkoxy of from one to six carbon atoms, or (k5d) halogen, (k6) phenoxy, optionally substituted with (k6a) alkyl of from one to six carbon atoms, (k6b) haloalkyl of from one to six carbon atoms, (k6c) alkoxy of from one to six carbon atoms, or (k6d) halogen, (k7) phenylthio, optionally substituted with (k7a) alkyl of from one to six carbon atoms, (k7b) haloalkyl of from one to six carbon atoms, (k7c) alkoxy of from one to six carbon atoms, or (k7d) halogen, (k8) 2-, 3-, or 4-pyridyl, optionally substituted with (k8a) alkyl of from one to six carbon atoms, (k8b) haloalkyl of from one to six carbon atoms, (k8c) alkoxy of from one to six carbon atoms, or (k8d) halogen; (k9) 2-, 3-, or 4-pyridyloxy, optionally substituted with (k9a) alkyl of from one to six carbon atoms, (k9b) haloalkyl of from one to six carbon atoms, (k9c) alkoxy of from one to six carbon atoms, or (k9d) halogen; and (1) 2- or 3-benzo[b]thienyl, optionally substituted with (l1) alkyl of from one to six carbon atoms, (l2) haloalkyl of from one to six carbon atoms; (l3) alkoxyl of from one to six carbon atoms, or (l4) halogen.

In another embodiment, the present invention provides pharmaceutical compositions which comprise a therapeutically effective amount of compound as defined above in combination with a pharmaceutically acceptable carrier.

In a still further embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH₂CH=CH—, —C(CH₃)=CH—, —CH₂CH=CHCH₂—, and the like.

The term "alkynyl" refers to a divalent group derived by the removal of two hydrogen atoms from a straight or branched chain acyclic hydrocarbon group containing a carbon-carbon triple bond.

The term "alkanoyl" represents an alkyl group, as defined above, attached to the parent molecular moiety through a carbonyl group. Alkanoyl groups are exemplified by acetyl, propionyl, butanoyl and the like.

The term "carbocyclic aryl" denotes a monovalent carbocyclic ring group derived by the removal of a single hydrogen atom from a monocyclic or bicyclic fused or non-fused ring system obeying the "4n+2π electron" or Huckel aromaticity rule. Examples of carbocyclic aryl groups include phenyl, 1-and 2-naphthyl, biphenyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moiety through a sulfur atom and thence through an alkylene group and are typified by phenylthiomethyl, 1- and 2-naphthylthioethyl and the like.

The term "metabolically cleavable group" denotes a group which is cleaved in vivo to yield the parent molecule of the structural formulae indicated above wherein M is hydrogen. Examples of metabolically cleavable groups include —COR, —COOR, —CONRR and —CH₂OR radicals where R is selected independently at each occurrence from alkyl, trialkylsilyl, carbocyclic aryl or carbocyclic aryl substituted with one or more of $C_1$-$C_4$ alkyl, halogen, hydroxy or $C_1$-$C_4$ alkoxy. Specific examples of representative metabolically cleavable groups include acetyl, methoxycarbonyl, benzoyl, methoxymethyl and trimethylsilyl groups.

PREFERRED EMBODIMENTS

Preferred compounds of the present invention are those having the structure

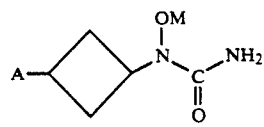

where the values of A and M are as defined above. Particular compounds falling within the scope of the present invention include, but are not limited to:

N-[3-(3-(4-fluorophenoxy)phenyl)-cyclobutyl]-N-hydroxyurea;

N-[3-phenylcyclobutyl]-N-hydroxyurea;

N-[3-(5-(4-fluorophenoxy)thien-2yl)-cyclobutyl]-N-hydroxyurea;

N-[3-(6-methoxy-2-naphthyl)-cyclobutyl]-N-hydroxyurea;

N-[3-(4-biphenyl)-cyclobutyl]-N-hydroxyurea;

N-[3-(3-methoxyphenyl)-cyclobutyl]-N-hydroxyacetamide;

and compounds having the names above wherein the N-hydroxy hydrogen atom is replaced by a pharmaceutically acceptable cation, or a pharmaceutically acceptable metabolically cleavable group.

Certain compounds of this invention may exist in either cis or trans isomers with respect to the relationship of the two groups attached to the cyclobutyl ring in addition to stereoisomeric forms by virtue of the presence of one or more chiral centers. The present invention contemplates all such geometric and stereoisomers, including R- and S-enantiomers, diastereomers, and cis/trans mixtures thereof as falling within the scope of the invention. If a particular enantiomer is desired, it may be prepared by chiral synthesis or by derivatization with a chiral auxiliary where the resulting diastereomeric mixture is separated and the auxiliary group cleaved to provide the pure desired enantiomers.

Lipoxygenase Inhibition Determination

Inhibition of leukotriene biosynthesis was evaluated in an assay, involving calcium ionophore-induced LTB₄ biosynthesis expressed human whole blood. Human heparinized whole blood was preincubated with test compounds or vehicle for 15 min at 37° C. followed by calcium ionophore A23187 challenge (final concentration of 8.3 μM) and the reaction terminated after 30 min by adding two volumes of methanol containing prostaglandin B₂ as an internal recovery standard. The methanol extract was analyzed for LTB₄ using a commercially available radioimmunoassay.

The compounds of this invention inhibit leukotriene biosynthesis as illustrated in Table 1.

TABLE 1

In Vitro Inhibitory Potencies of Compounds of this Invention Against 5-Lipoxygenase from Stimulated LTB₄ Formation in Human Whole Blood

| Example | IC$_{50}$ (10$^{-6}$M) |
|---|---|
| 1a | 0.13 |
| 1b | 0.16 |
| 2a | 0.33 |
| 2b | 0.30 |
| 3a | 53% @ 0.1 |
| 3b | 52% @ 0.1 |
| 4a | 0.23 |
| 4b | 0.52 |
| 5a | 0.09 |
| 5b | 0.96 |
| 6a | 0.51 |

TABLE 1-continued

In Vitro Inhibitory Potencies of Compounds of this Invention Against 5-Lipoxygenase from Stimulated $LTB_4$ Formation in Human Whole Blood

| Example | $IC_{50}$ ($10^{-6}$M) |
| --- | --- |
| 6b | 1.21 |

Inhibition of Leukotriene Biosynthesis

Inhibition of the biosynthesis of leukotrienes in vivo after oral administration of compound was determined using a rat peritoneal anaphylaxis model in a similar manner as that described by Yound and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results are presented in Table 2.

TABLE 2

In Vivo Inhibitory Potencies of Compounds of this Invention

| Example | Percent Inhibition of Leukotriene Biosynthesis at 30 μM/kg |
| --- | --- |
| 1a | 76 |
| 1b | 59 |
| 2a | 51 |
| 2b | 45 |
| 3b | 82 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of this invention can be prepared as is illustrated in Scheme I.

Scheme 1

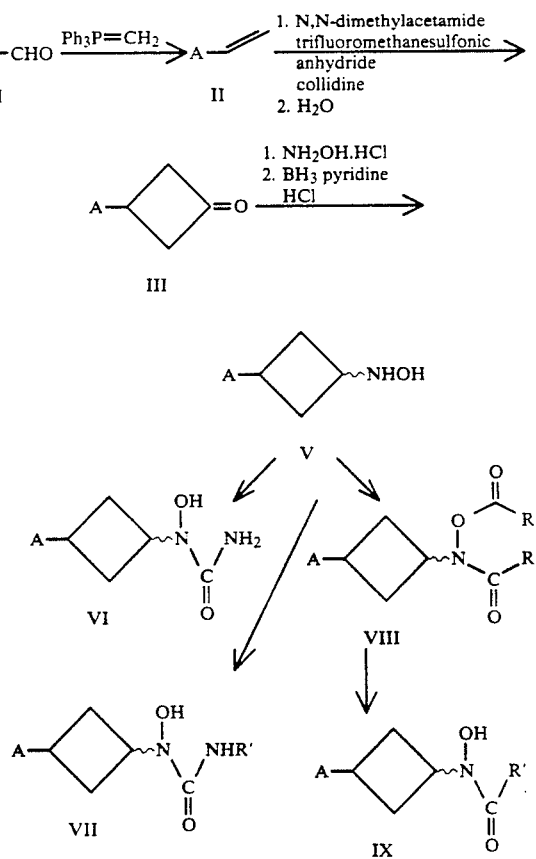

The starting aldehyde I is converted by known methods such as the Wittig reaction to the corresponding olefin II which is then transformed into the requisite cyclobutanone III by known methods such as that reported using a mixture of N,N-dimethylacetamide, trifluoromethansulfonic anhydride, and collidine (J. Am. Chem. Soc. 1985, 107, 2192). The cyclobutanone is then transformed into the corresponding oxime IV which is reduced with borane pyridine to the hydroxylamine intermediate V. The hydroxylamine intermediate V is converted to the desired N-hydroxyureas VI by known methods such as treatment with HCNO, TMS-CNO, or substituted N-hydroxyureas VII with substituted isocyanates (R'CNO). The intermediate V is converted to hydroxamic acids by treatment with acylhalide or anhydride to provide the diacyl derivative VIII which is treated with hydroxide to provide the desired hydroxamic acids IX.

The cyclobutyl $N$-hydroxyurea and hydroxamic acid compounds VI, VII and IX can exist as a mixture of geometric isomers where the substituents project on the same face of the cyclobutyl ring (syn- or Z-isomer) or opposite to each other (anti- or E-isomer). A method to separate these isomers is illustrated in Scheme 2. Treatment of the isomeric mixture with 4-chlorobenzoic acid and dicyclohexylcarbodiimide (DCC) provides the O-acyl adducts X and XI which can be physically separated by chromatography. The 4-chlorobenzoyl group is then removed to provide the pure E-isomer XII or the pure Z-isomer XIII.

Scheme 2

To a suspension of potassium tert-butoxide (2.61 g, 23.3 mmol) in ether (100 mL) was added methyltriphenylphosphonium bromide (8.34 g, 23.3 mmol) and the solution was brought to reflux for 15 min. It was then cooled to 0° C. and 3-(4-fluorophenoxy)benzaldehyde (4.80 g, 22.2 mmol) was added. The reaction was stirred for 5 min at 0° C., the cooling bath was withdrawn and the reaction allowed to warm to ambient temperature and stir for 45 min. It was then filtered through Celite and concentrated. The resulting residue was chromatographed (silica gel; hexanes, ether 96:4) to afford 4.09 g (86%) of 3-(4-fluorophenoxy)styrene as a colorless oil.

To a solution of N,N-dimethylacetamide (1.66 g, 19.1 mmol) in dichloroethane (50 mL) at −15° C., was added trifluoromethanesulfonic anhydride (5.39 g, 19.1 mmol) dropwise and the mixture was stirred for 5 min. A mixture of 3-(4-fluorophenoxy)styrene (4.08 g, 19.1 mmol) and collidine (2.31 g, 19.1 mmol) as a solution in dichloroethane (10 mL) was then added dropwise. Upon completion of addition, the cooling bath was withdrawn and the reaction allowed to warm to ambient temperature, then further brought to reflux for 18 hours. Water (20 mL) was then added and the reaction was kept at reflux for an additional 5 hours. It was then cooled to ambient temperature and the layers were separated. The organic phase was washed with 10% aqueous HCl (50 mL) and water (50 mL). It was then dried over MgSO4 and concentrated. The resulting residue was chromatographed (silica gel; hexanes, ether

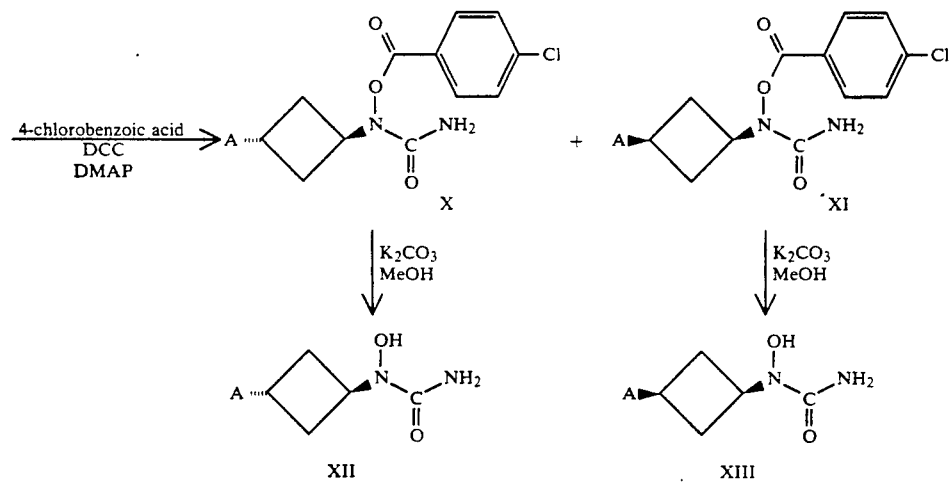

EXAMPLE 1

Preparation of N-[3-(3-(4-fluorophenoxy)phenyl)-cyclobutyl]-N-hydroxyurea

A mixture of 3-hydroxybenzaldehyde (24.37 g, 199.6 mmol), 4-bromofluorobenzene (69.86 g, 399.2 mmol), potassium carbonate (42.76 g, 309.4 mnmol) and copper powder (6.34 g, 99.8 mmol) in pyridine (200 mL) was refluxed for 64 hours. It was then cooled to ambient temperature and filtered through Celite. The filtrate was diluted with ethyl acetate (600 mL) and washed with water (3×400 mL). The organic phase was dried over MgSO4. The resulting residue was chromatographed (silica gel; hexanes, ether 85:15) to afford 31.03 g (72%) of 3-(4-fluorophenoxy)benzaldehyde as a pale yellow solid.

90:10) to afford 2.60 g (53%) of 3-(3-(4-fluorophenoxy)-phenyl)cyclobutanone as a colorless oil.

A solution of 3-(3-(4-fluorophenoxy)phenyl)cyclobutanone (2.59 g, 10.1 mmol) and hydroxylamine hydrochloride (844 mg, 12.1 mmol) in 1:1 ethanol:pyridine (50 mL) was stirred for 36 hours. It was then concentrated in vacuo. The residue was taken up in brine (50 mL) and extracted with ethyl acetate (3×50 mL). The organics were combined, dried over MgSO4 and concentrated to afford 3-(3-(4-fluorophenoxy)phenyl)-cyclobutanone oxime which was used as is.

To a solution of 3-(3-(4-fluorophenoxy)phenyl)cyclobutanone oxime from above, in ethanol (50 mL) was added borane.pyridine (2.06 g, 22.2 mmol) and the resulting solution was stirred for 30 min. 6N aqueous HCl (5.05 mL, 30.3 mmol) was then added dropwise and the reaction was stirred for 30 min. It was then neutralized by the addition of 2N aqueous NaOH and the ethanol evaporated in vacuo. The resulting residue was further diluted with brine to a volume of approximately 50 mL and extracted with ethyl acetate (3×50 mL). The organics were combined, dried over MgSO$_4$ and concentrated to afford 3-(3-(4-flurophenoxy)phenyl)-1-cyclobutylhydroxylamine which was used as is.

To a solution of 3-(3-(4-fluorophenoxy)phenyl)-1-cyclobutylhydroxylamine from above in THF (50 mL) was added trimethylsilylisocyanate (1.64 g of 85% purity, 12.12 mmol) and the reaction was stirred for 10 min. It was then concentrated in vacuo. The resulting residue was chromatographed (silica gel; ether, methanol 96:4 to 90:10) to afford 1.60 g (50% over three steps) of N-[3-(3-(4-fluorophenoxy)phenyl)-cyclobutyl]-N-hydroxyurea as a 1:1 mixture of diastereomers.

To a solution of N-[3-(3-(4-fluorophenoxy)phenyl)-cyclobutyl]-N-hydroxyurea (1.57 g, 5.0 mmol) from above, and 4-chlorobenzoic acid (783 mg, 5.0 mmol) in CH$_2$Cl$_2$ (25 mL) was added dicyclohexylcarbodiimide (1.23 g, 6.0 mmol) followed by a crystal of 4-N,N-dimethylaminopyridine and the reaction was stirred for 18 hours. It was then filtered through Celite and concentrated. The resulting residue was chromatographed (silica gel; CH$_2$Cl$_2$, ether 92.5:7.5) to afford 618 mg of the less polar diastereomer and 629 mg of the more polar diastereomer of N-(4-chlorobenzoate)-N-(3-(3-(4-fluorophenoxy)phenyl)-1-cyclobutyl)urea along with some mixed fractions.

To a solution of the less polar diasteromer of N-(4-chlorobenzoate)-N-(3-(3-(4-fluorophenoxy)phenyl)-1-cyclobutyl)urea (608 mg, 1.29 mmol) in methanol (6 mL) was added potassium carbonate (179 mg, 1.29 mmol) and the reaction was stirred for 20 min. The solution was then decanted and concentrated. The residue was chromatographed (silica gel; 94:6 ether, methanol) followed by crystallization in ethyl acetate/hexanes to afford N-[3-(3-(4-fluorophenoxy)phenyl)-cyclobutyl]-N-hydroxyurea, 1a, as a single diastereomer. m.p.=117.0°-118.5° C.; $^1$H NMR (300 MHz, DMSO-d$_6$): 2.15 (m, 2H), 2.68 (m, 2H), 3.37 (m, 1H), 4.77 (pentet, 1H), 6.33 (bs, 2H), 6.77 (m, 1H), 6.93 (m, 1H), 7.08 (m, 3H), 7.23 (m, 2H), 7.32 (t, 1H, J=8.5 Hz), 9.27 (s, 1H); MS (M+NH$_4$)$^+$=334; Analysis calc'd for C$_{17}$H$_{17}$FN$_2$O$_3$: C, 64.54, H, 5.42, N, 8.86; Found: C, 64.32, H, 5.44, N, 8.76.

The other diasteremer of N-[3-(3-(4-fluorophenoxy)phenyl)-cyclobutyl]-N-hydroxyurea, 1b, was prepared according to the previous procedure using the more polar diastereomer of N-(4-chlorobenzoate)-N-(3-(3-(4-fluorophenoxy)phenyl)-1-cyclobutyl)urea instead of the less polar diastereomer. m.p.=151.5°-152.5° C.; $^1$H NMR (300 MHz, DMSO-d$_6$): 2.32 (m, 4H), 3.06 (m, 1H), 4.63 (m, 1H), 6.29 (bs, 2H), 6.76 (m, 1H), 6.86 (m, 1H), 6.98-7.09 (m, 3H), 7.22 (m, 2H), 7.30 (t, 1H, J=8 HZ), 9.17 (s, 1H); MS (M+H)$^+$=317; Analysis calc'd for C$_{17}$H$_{17}$FN$_2$O$_3$: C, 64.54, H, 5.42, N, 8.86; Found: C, 64.55, H, 5.47, N, 8.85.

EXAMPLE 2

Preparation of N-[3-phenylcyclobutyl]-N-hydroxyurea

The two diastereomeric materials were prepared in the same manner as Example 1 substituting styrene for 3-(4-fluorophenoxy)styrene.

2a: m.p.=167.5°-169.0° C.; $^1$H NMR (300 MHz, DMSO-d$_6$): 2.35 (m, 4H), 3.07 (m, 1H), 4.65 (m, 1H), 6.28 (bs, 2H), 7.14-7.34 (m, 5H), 9.8 (s, 1H); MS (M+H)$^+$=207; Analysis cacl'd for C$_{11}$H$_{14}$N$_2$O$_2$: C, 64.06, H, 6.84, N, 13.59. Found: C, 63.98, H, 6.88, N, 13.55.

2b: m.p.=149°-150° C.; $^1$H NMR (300 MHz, DMSO-d$_6$): 2.16 (m, 2H), 2.60 (m, 2H), 3.38 (m, 1H), 4.81 (m, 1H), 6.33 (bs, 2H), 7.19 (m, 1H), 7.32 (m, 4H), 9.27 (s, 1H); MS (M+H)$^+$=207; Analysis calc'd for C$_{11}$H$_{14}$N$_2$O$_2$: C, 64.06, H, 6.84, N, 13.59; Found: C, 63.89, H, 6.83, N, 13.56.

EXAMPLE 3

Preparation of N-[3-(5-(4-fluorophenoxy)thien-2-yl)-cyclobutyl]-N-hydroxyurea

A solution of 4-fluorophenol (22.42 g, 200 mmol), 2-bromothiophene (65.22 g, 400 mmol), potassium carbonate (42.84 g, 310 mmol), and copper powder (6.35 g, 100 mmol) in pyridine (200 mL) was refluxed for 18 hours. It was then cooled to ambient temperature and filtered through Celite. The filtrate was diluted with ethyl acetate (500 mL) and washed with water (3×300 mL). The organic phase was dried over MgSO$_4$ and concentrated. The resulting residue was chromatographed (silica gel; hexanes) to afford 3.67 g (9%) of 2-(4-fluorophenoxy)thiophene as a colorless oil.

To a solution of 2-(4-fluorophenoxy)thiophene (3.66 g, 18.9 mmol) in THF (90 mL) at −78° C., was added butyllithium (7.5 ml of a 2.5M solution in hexanes, 18.9 mmol) dropwise. Upon completion of addition, the mixture was stirred for 20 min. N,N-Dimethylformamide (1.52 g, 20.8 mmol) was then added and the reaction was stirred for 40 min at −78° C. It was then quenched with saturated aqueous NH$_4$Cl (100 mL) and extracted with ethyl acetate (3×100 mL). The organics were combined, dried over MgSO$_4$ and concentrated. The resulting residue was chromatographed (silica gel; 3:1 hexanes, ether) to afford 3.59 g (86%) of 5-(4-fluorophenoxy)-2-thiophenecarboxaldehyde as a slightly orange solid.

The two diastereomeric materials were prepared in the same manner as Example 1 substituting 5-(4-fluorophenoxy)-2-thiophene carboxaldehyde for 3-(4-fluorophenoxy)benzaldehyde.

3a: m.p.=153°-155° C.; $^1$H NMR (300 MHz, DMSO-d$_6$): 2.13 (m, 2H), 2.68 (m, 2H), 3.43 (m, 1H), 4.82 (m, 2H), 6.35 (bs, 2H), 6.49 (d, 1H, J=4 Hz), 6.70 (dd, 1H, J=4 Hz, J=1 Hz), 7.12-7.27 (m, 4H), 9.26 (s, 1H); MS (M+H)$^+$=323; Analysis calc'd for C$_{15}$H$_{15}$FN$_2$O$_3$S: C, 55.89, H, 4.69, N, 8.69; Found: C, 55.83, H, 4.78, N, 8.61.

3b: m.p.=148°-150° C.; $^1$H NMR (300 MHz, DMSO-d$_6$): 2.11-2.44 (m, 4H), 3.18 (m, 1H), 4.59 (m, 1H), 6.31 (bs, 2H), 6.46 (d, 1H, J=4 Hz), 6.58 (dd, 1H, J=4 Hz, J=1 Hz), 7.11-7.27 (m, 4H), 9.18 (s, 1H); MS (M+H)$^+$=323; Analysis calc'd for C$_{15}$H$_{15}$FN$_2$O$_3$S: C, 55.89, H, 4.69, N, 8.69; Found: C, 55.63, H, 4.67, N, 8.64.

EXAMPLE 4

Preparation of N-[3-(6-methoxy-2-naphthyl)-cyclobutyl]-N-hydroxyurea

To a solution of butyllithium (50.6 ml of a 2.5M solution in hexanes, 126.5 mmol) in THF (200 mL) at −78° C., was added 2-bromo-6-methoxynaphthalene (15.00 g, 63.3 mmol) portionwise. Upon completion of addition, the mixture was stirred for 30 min at −78° C. N,N-Dimethylformamide (6.94 g, 94.95 mmol) was added dropwise. The cooling bath was withdrawn and the reaction allowed to warm to ambient temperature. It was then quenched with saturated aqueous NH₄Cl (200 mL) and the THF was stripped off in vacuo. The aqueous residue was extracted with ethyl acetate (3×200 mL). The organics were combined, dried over MgSO₄ and concentrated. The resulting residue was chromatographed (silica gel; 1:4 ether, hexanes) to afford 8.86 g (75%) of 6-methoxy-2-naphthalenecarboxaldehyde as a pale yellow solid.

The two diastereometic materials were prepared in the same manner as Example 1 substituting 6-methoxy-2-naphthalenecarboxaldehyde for 3-(4-fluorophenoxy)-benzaldehyde.

4a: m.p.=169.5°-170.0° C.; ¹H NMR (300 MHz, DMSO-d₆): 2.25 (m, 2H), 2.76 (m, 2H), 3.51 (m, 1H), 3.86 (s, 3H), 4.87 (pentet, 1H), 6.34 (bs, 2H), 7.13 (dd, 1H, J=3 Hz, J=8.5 Hz), 7.28 (d, 1H, J=3 Hz), 7.41 (dd, 1H, J=2 Hz, J=8.5 Hz), 7.78 (m, 3H), 9.32 (s, 1H); ... (M+H)⁺=287; Analysis calc'd for C₁₆H₁₈N₂O₃.¼H₂O: C, 66.07, H, 6.41, N, 9.63; Found: C, 65.93, H, 6.18, N, 9.65.

4b: m.p.=186°-188° C.; ¹H NMR (300 MHz, DMSO-d₆): 2.38 (m, 4H), 3.16 (m, 1H), 3.81 (s, 3H), 4.65 (pentet, 1H), 6.26 (bs, 2H), 7.09 (dd, 1H, J=2.5 Hz, J=9 Hz), 7.23 (d, 1H, J=2.5 Hz), 7.34 (dd, 1H, J=1.5 Hz, J=9 Hz), 7.56 (m, 1H), 7.72 (d, 2H, J=9 Hz), 9.17 (s, 1H); MS (M+NH₄)⁺=304.

EXAMPLE 5

Preparation of
N-[3-(4-biphenyl)-cyclobutyl]-N-hydroxyurea

The two diastereomeric materials were prepared in the same manner as Example 1 substituting 4-biphenylcarboxaldehyde for 3-(4-fluorophenoxy)benzaldehyde.

5a: m.p.=185°-187° C.; ¹H NMR (300 MHz, DMSO-d₆): 2.20 (m, 2H), 2.73 (m, 2H), 3.43 (m, 1H), 4.85 (m, 1H), 6.34 (bs, 2H), 7.30-7.50 (m, 5H), 7.63 (m, 4H), 9.29 (s, 1H); MS (M+H)⁺=283.

5b: m.p.=195° C. (dec); ¹H NMR (300 MHz, DMSO-d₆): 2.38 (m, 4H), 3.12 (m, 1H), 4.68 (m, 1H), 6.30 (bs, 2H), 7.33 (m, 3H), 7.46 (m, 2H), 7.63 (m, 4H), 9.22 (s, 1H); MS (M+H)⁻=283; Analysis calc'd for C₁₇H₁₈N₂O₂: C, 72.32, H, 6.43, N, 9.92; Found: C, 72.26, H, 6.21, N, 9.62.

EXAMPLE 6

Preparation of
N-[3-(3-methoxyphenyl)cyclobutyl]-N-hydroxyacetamide

To a solution of 3-(3-methoxyphenyl)cyclobutylhydroxylamine (34.8 mmol), prepared according to the procedure described in Example 1 substituting 3-methoxybenzaldehyde for 3-(4-fluorophenoxy)benzaldehyde, in CH₂Cl₂ (150 mL) at 0° C., was added acetyl chloride (8.20 g, 104.4 mmol) followed by the dropwise addition of triethylamine and a few crystals of N,N-dimethylaminopyridine. The cooling bath was withdrawn and the reaction allowed to warm to ambient temperature. It was then diluted with brine (100 mL) and the layers were separated. The aqueous phase was extracted with CH₂Cl₂ (2×100 mL). The organics were combined, dried over MgSO₄ and concentrated to afford crude N-acetoxy-N-[3-(3-methoxyphenyl)cyclobutyl]-acetamide.

To a solution of N-acetoxy-N-[3-(3-methoxyphenyl)cyclobutyl]acetamide, (34.8 mmol from above), in methanol (150 mL) was added K₂CO₃ (9.22 g, 69.6 mmol) and the heterogeneous mixture was stirred for 30 min. An additional portion of K₂CO₃ (4.50 g) was then added and the reaction was stirred an additional 30 min. It was then filtered through Celite and concentrated. The resulting residue was chromatographed (silica gel; ether) to afford 4.92 g (60% over four steps) of N-[3-(3-methoxyphenyl)cyclobutyl]-N-hydroxyacetamide as an orange oil.

The two diastereomeric materials were separated in the same manner as Example 1 substituting N-[3-(3-methoxyphenyl)cyclobutyl]-N-hydroxyacetamide for N-[3-(3-(4-fluorophenoxy)phenyl)-cyclobutyl]-N-hydroxyurea.

6a: m.p.=72°-73° C.; ¹H NMR (300 MHz, DMSO-d₆): 1.96 (s, 3H), 2.19 (m, 2H), 2.67 (m, 2H), 3.38 (m, 1H), 3.71 (s, 3H), 5.02 (m, 1H), 6.70-6.87 (m, 3H), 7.20 (t, 1H, J=8 Hz), 9.70 (bs, 1H); MS (M+H)⁺=236; Analysis calc'd for C₁₃H₁₇NO₃: C, 66.36, H, 7.29, N, 5.95; Found: C 66.72, H, 7.39, N, 6.12.

6b: ¹H NMR (300 MHz, DMSO-d₆): 1.95 (s, 3H), 2.34 (m, 4H), 3.06 (m, 1H), 3.70 (s, 3H), 4.88 (m, 1H), 6.74 (m, 3H), 7.18 (t, 1H, J=8 Hz), 9.62 (bs, 1H); MS (M+NH₄)⁺=253; Analysis calc'd for C₁₃H₁₇NO₃: C, 66.36, H, 7.29, N, 5.95; Found: C 66.47, H, 7.64, N, 6.17.

The compounds represented in Table I can be prepared by the method as described in Example 1 substituting the appropriate aldehyde precursor shown by molecular formula instead of 3-(4-fluorophenoxy)benzaldehyde to provide the desired cyclobutyl-N-hydroxyurea product as shown by molecular formula.

TABLE I

| | Aldehyde Precursor | Product |
|---|---|---|
| Example 7 | thiophene-CHO | thiophene-cyclobutyl-N(OH)-C(O)-NH₂ |

TABLE I-continued

| | Aldehyde Precursor | Product |
|---|---|---|
| Example 8 | thiophene-3-carboxaldehyde | 1-[3-(thiophen-3-yl)cyclobutyl]-1-hydroxyurea |
| Example 9 | 5-methylthiophene-2-carboxaldehyde | 1-[3-(5-methylthiophen-2-yl)cyclobutyl]-1-hydroxyurea |
| Example 10 | 5-bromothiophene-2-carboxaldehyde | 1-[3-(5-bromothiophen-2-yl)cyclobutyl]-1-hydroxyurea |
| Example 11 | 5-bromothiophene-2-carboxaldehyde | 1-[3-(5-bromothiophen-2-yl)cyclobutyl]-1-hydroxyurea |
| Example 12 | thiophene-2-carboxaldehyde | 1-[3-(thiophen-2-yl)cyclobutyl]-1-hydroxyurea |
| Example 13 | thiophene-3-carboxaldehyde | 1-[3-(thiophen-3-yl)cyclobutyl]-1-hydroxyurea |
| Example 14 | 5-methylthiophene-2-carboxaldehyde | 1-[3-(5-methylthiophen-2-yl)cyclobutyl]-1-hydroxyurea |

TABLE I-continued

| | Aldehyde Precursor | Product |
|---|---|---|
| Example 15 | 3-phenoxybenzaldehyde (PhO-C6H4-CHO) | 3-(3-phenoxyphenyl)cyclobutyl-N-hydroxyurea |
| Example 16 | 3-(4-chlorophenoxy)benzaldehyde | 3-[3-(4-chlorophenoxy)phenyl]cyclobutyl-N-hydroxyurea |
| Example 17 | 3-(4-methylphenoxy)benzaldehyde | 3-[3-(4-methylphenoxy)phenyl]cyclobutyl-N-hydroxyurea |
| Example 18 | 3-(4-methoxyphenoxy)benzaldehyde | 3-[3-(4-methoxyphenoxy)phenyl]cyclobutyl-N-hydroxyurea |
| Example 19 | 3-(2-pyridyloxy)benzaldehyde | 3-[3-(2-pyridyloxy)phenyl]cyclobutyl-N-hydroxyurea |
| Example 20 | 3-(4-pyridyloxy)benzaldehyde | 3-[3-(4-pyridyloxy)phenyl]cyclobutyl-N-hydroxyurea |
| Example 21 | 2-phenoxybenzaldehyde | 3-(2-phenoxyphenyl)cyclobutyl-N-hydroxyurea |

TABLE I-continued

| | Aldehyde Precursor | Product |
|---|---|---|
| Example 22 | 4-PhO-C6H4-CHO | 4-PhO-phenyl cyclobutyl N(OH)C(O)NH2 |
| Example 23 | 4-CH3-C6H4-CHO | 4-CH3-phenyl cyclobutyl N(OH)C(O)NH2 |
| Example 24 | 4-Br-C6H4-CHO | 4-Br-phenyl cyclobutyl N(OH)C(O)NH2 |
| Example 25 | 4-CH3O-C6H4-CHO | 4-Br-phenyl cyclobutyl N(OH)C(O)NH2 |
| Example 26 | 4-isobutyl-C6H4-CHO | 4-isobutyl-phenyl cyclobutyl N(OH)C(O)NH2 |
| Example 27 | pyridine-2-CHO | 2-pyridyl cyclobutyl N(OH)C(O)NH2 |
| Example 28 | 6-CH3-pyridine-2-CHO | 6-CH3-2-pyridyl cyclobutyl N(OH)C(O)NH2 |

TABLE I-continued

| | Aldehyde Precursor | Product |
|---|---|---|
| Example 29 | pyridine-3-carboxaldehyde | 3-pyridyl-cyclobutyl-N-hydroxyurea |
| Example 30 | pyridine-4-carboxaldehyde | 4-pyridyl-cyclobutyl-N-hydroxyurea |
| Example 31 | benzo[b]thiophene-2-carboxaldehyde | benzo[b]thiophene-2-yl-cyclobutyl-N-hydroxyurea |
| Example 32 | benzofuran-2-carboxaldehyde | benzofuran-2-yl-cyclobutyl-N-hydroxyurea |
| Example 33 | naphthalene-2-carboxaldehyde | naphthalen-2-yl-cyclobutyl-N-hydroxyurea |
| Example 34 | naphthalene-1-carboxaldehyde | naphthalen-1-yl-cyclobutyl-N-hydroxyurea |
| Example 35 | 5-butoxythiophene-2-carboxaldehyde | 5-butoxythiophen-2-yl-cyclobutyl-N-hydroxyurea |

TABLE I-continued

| | Aldehyde Precursor | Product |
|---|---|---|
| Example 36 | 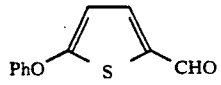 | 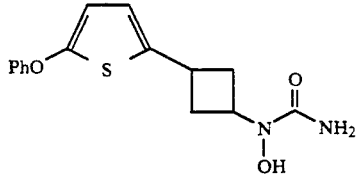 |
| Example 37 | 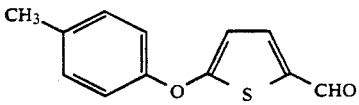 | 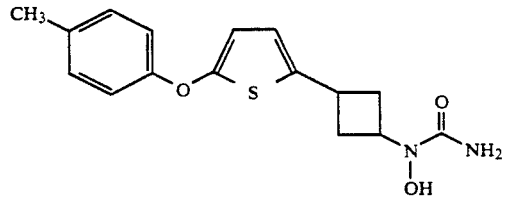 |
| Example 38 | 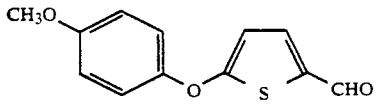 | 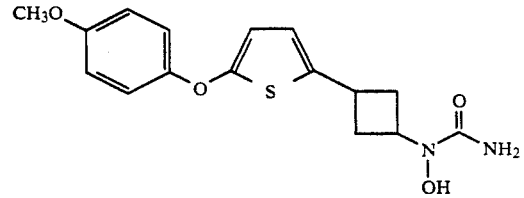 |
| Example 39 | 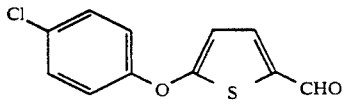 | 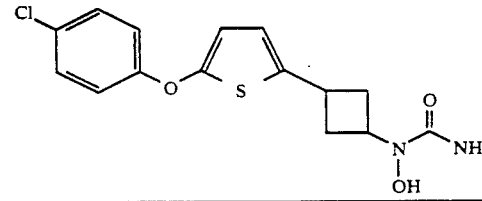 |

The compounds represented in Table II can be prepared by the method as described in Example 1 substituting the appropriate aldehyde precursor shown by molecular formula instead of 3-(4-fluorophenoxy)benzaldehyde and utilizing the requisite substituted isocyanate to prepare the corresponding substituted cyclobutyl-N-hydroxyurea product as shown by molecular formula.

TABLE II

| | Aldehyde Precursor | Product |
|---|---|---|
| Example 40 | 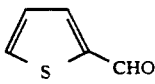 | 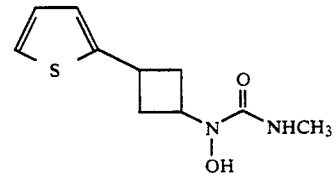 |
| Example 41 | 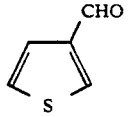 | 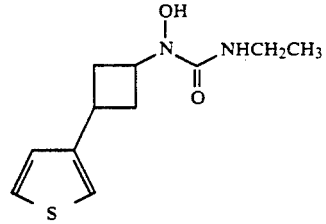 |

TABLE II-continued

| | Aldehyde Precursor | Product |
|---|---|---|
| Example 42 | 5-bromothiophene-2-carbaldehyde | 5-bromothiophen-2-yl cyclobutyl N-hydroxy-N'-phenylurea |
| Example 43 | 5-bromothiophene-2-carbaldehyde | 5-bromothiophen-2-yl cyclobutyl N-hydroxy-N'-butylurea (NHC$_4$H$_9$) |
| Example 44 | 5-bromothiophene-2-carbaldehyde | 5-bromothiophen-2-yl cyclobutyl N-hydroxy-N'-benzylurea (NHCH$_2$C$_6$H$_5$) |
| Example 45 | thiophene-2-carbaldehyde | thiophen-2-yl cyclobutyl N-hydroxy-N'-tert-butylurea (NHtC$_4$H$_9$) |
| Example 46 | thiophene-3-carbaldehyde | bis-thiophen-3-yl cyclobutyl N-hydroxy-N'-methylurea (NHCH$_3$) |
| Example 47 | 5-methylthiophene-2-carbaldehyde | 5-methylthiophen-2-yl cyclobutyl N-hydroxy-N'-phenylurea (NHC$_5$H$_6$) |
| Example 48 | 3-phenoxybenzaldehyde (PhO-CHO) | 3-phenoxyphenyl cyclobutyl N-hydroxy-N'-(2-methoxyethyl)urea (NHCH$_2$CH$_2$OCH$_3$) |
| Example 49 | 3-(4-chlorophenoxy)benzaldehyde | 3-(4-chlorophenoxy)phenyl cyclobutyl N-hydroxy-N'-methylurea (NHCH$_3$) |

TABLE II-continued
| | Aldehyde Precursor | Product |
|---|---|---|
| Example 50 | 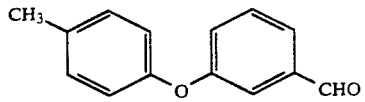 | 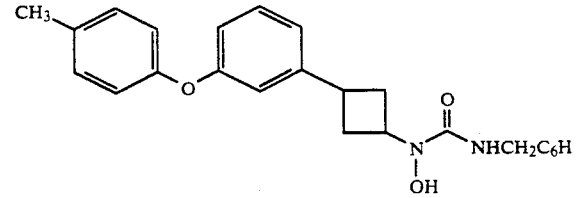 |
| Example 51 |  | 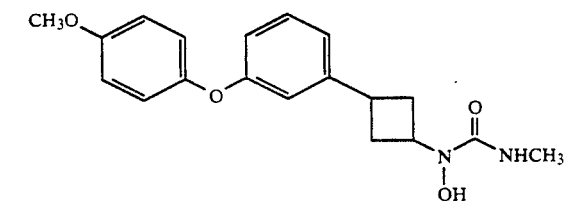 |
| Example 52 | 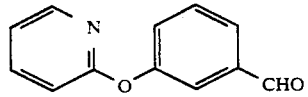 | 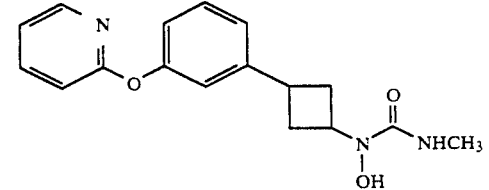 |
| Example 53 | 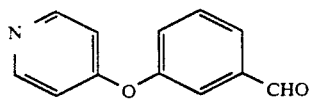 | 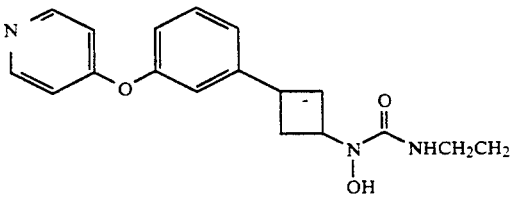 |
| Example 54 | 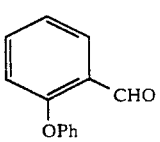 | 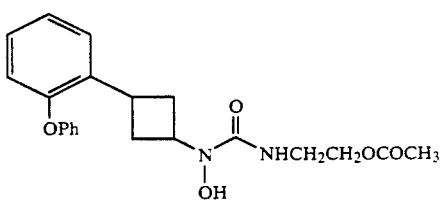 |
| Example 55 | 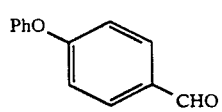 | 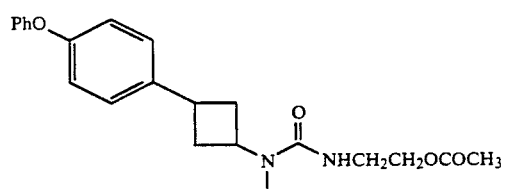 |
| Example 56 | 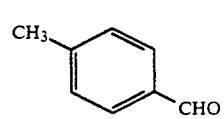 | 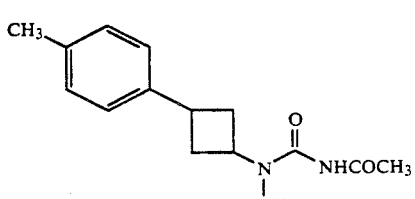 |

TABLE II-continued

| | Aldehyde Precursor | Product |
|---|---|---|
| Example 57 | 4-Br-C6H4-CHO | 4-Br-C6H4-cyclobutyl-N(OH)-C(O)-NHCOCH3 |
| Example 58 | 4-CH3O-C6H4-CHO | 4-CH3O-C6H4-cyclobutyl-N(OH)-C(O)-NHCOCH3 |
| Example 59 | 4-(iBu)-C6H4-CHO | 4-(iBu)-C6H4-cyclobutyl-N(OH)-C(O)-NHCH3 |
| Example 60 | pyridine-2-CHO | 2-pyridyl-cyclobutyl-N(OH)-C(O)-NHC6H5 |
| Example 61 | 6-CH3-pyridine-2-CHO | 6-CH3-2-pyridyl-cyclobutyl-N(OH)-C(O)-NHC6H5 |
| Example 62 | pyridine-3-CHO | 3-pyridyl-cyclobutyl-N(OH)-C(O)-NHCH2CH2OCOCH3 |
| Example 63 | pyridine-4-CHO | 4-pyridyl-cyclobutyl-N(OH)-C(O)-NHCH3 |

TABLE II-continued
| | Aldehyde Precursor | Product |
|---|---|---|
| Example 64 | 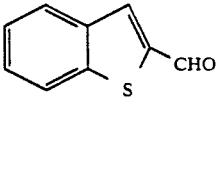 | 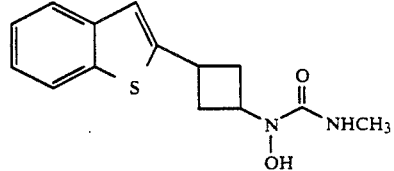 |
| Example 65 | 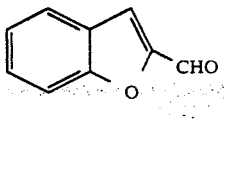 | 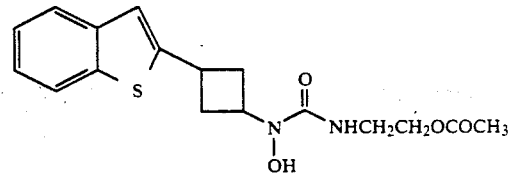 |
| Example 66 | 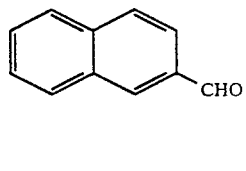 | 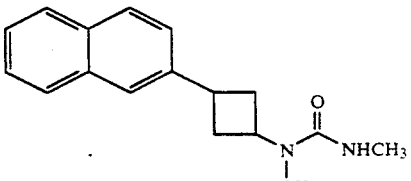 |
| Example 67 | 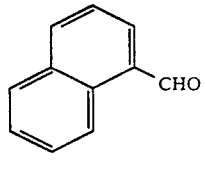 | 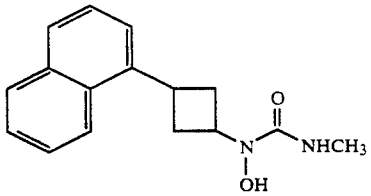 |
| Example 68 | 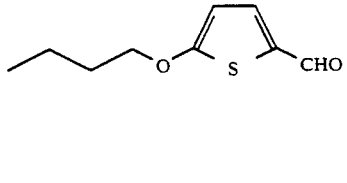 | 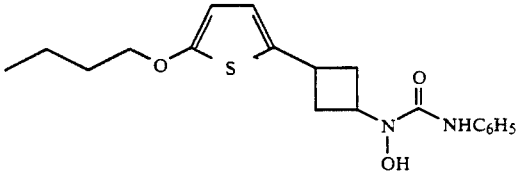 |
| Example 69 | 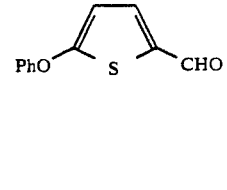 | 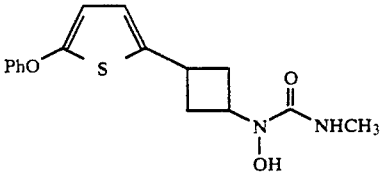 |
| Example 70 | 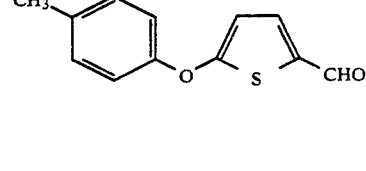 | 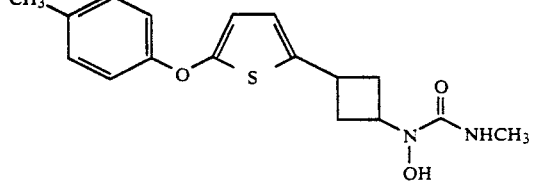 |

TABLE II-continued

| | Aldehyde Precursor | Product |
|---|---|---|
| Example 71 | 4-CH₃O-C₆H₄-O-[thiophene]-CHO | 4-CH₃O-C₆H₄-O-[thiophene]-cyclobutyl-N(OH)-C(=O)-NHCOCH₃ |
| Example 72 | 4-Cl-C₆H₄-O-[thiophene]-CHO | 4-Cl-C₆H₄-O-[thiophene]-cyclobutyl-N(OH)-C(=O)-NHC₆H₅ |

The compounds represented in Table III can be prepared by the method as described in Example 6 substituting the appropriate aldehyde precursor shown by molecular formula and the requisite acylchloride to provide the desired cyclobutylhydroxamic acid product as shown by molecular formula.

TABLE III

| | Aldehyde Precursor | Product |
|---|---|---|
| Example 73 | [thiophene-2]-CHO | [thiophene-2]-cyclobutyl-N(OH)-C(=O)-CH₃ |
| Example 74 | [thiophene-3]-CHO | [thiophene-3]-cyclobutyl-N(OH)-C(=O)-CH₂CH₃ |
| Example 75 | 5-CH₃-[thiophene-2]-CHO | 5-CH₃-[thiophene-2]-cyclobutyl-N(OH)-C(=O)-tC₄H₉ |
| Example 76 | 5-Br-[thiophene-2]-CHO | 5-Br-[thiophene-2]-cyclobutyl-N(OH)-C(=O)-C₆H₅ |
| Example 77 | 5-Br-[thiophene-2]-CHO | 5-Br-[thiophene-2]-cyclobutyl-N(OH)-C(=O)-CH₂C₆H₅ |

TABLE III-continued

| | Aldehyde Precursor | Product |
|---|---|---|
| Example 78 | 2-thiophenecarboxaldehyde | 3-(thiophen-2-yl)cyclobutyl-N-hydroxy-N-acetamide |
| Example 79 | 3-thiophenecarboxaldehyde | 3-(thiophen-3-yl)cyclobutyl-N-hydroxy-N-propanamide |
| Example 80 | 5-methyl-2-thiophenecarboxaldehyde | 3-(5-methylthiophen-2-yl)cyclobutyl-N-hydroxy-N-phenylacetamide |
| Example 81 | 3-phenoxybenzaldehyde | 3-(3-phenoxyphenyl)cyclobutyl-N-hydroxy-N-benzamide |
| Example 82 | 3-(4-chlorophenoxy)benzaldehyde | 3-[3-(4-chlorophenoxy)phenyl]cyclobutyl-N-hydroxy-N-propanamide |
| Example 83 | 3-(4-methylphenoxy)benzaldehyde | 3-[3-(4-methylphenoxy)phenyl]cyclobutyl-N-hydroxy-N-acetamide |
| Example 84 | 3-(4-methoxyphenoxy)benzaldehyde | 3-[3-(4-methoxyphenoxy)phenyl]cyclobutyl-N-hydroxy-N-acetamide |

TABLE III-continued

| | Aldehyde Precursor | Product |
|---|---|---|
| Example 85 | 2-(3-formylphenoxy)pyridine | 3-[3-(pyridin-2-yloxy)phenyl]cyclobutyl-N-hydroxy-N-acetamide |
| Example 86 | 4-(3-formylphenoxy)pyridine | 3-[3-(pyridin-4-yloxy)phenyl]cyclobutyl-N-hydroxy-N-acetamide |
| Example 87 | 2-phenoxybenzaldehyde | 3-(2-phenoxyphenyl)cyclobutyl-N-hydroxy-N-benzamide |
| Example 88 | 4-phenoxybenzaldehyde | 3-(4-phenoxyphenyl)cyclobutyl-N-hydroxy-N-acetamide |
| Example 89 | 4-methylbenzaldehyde | 3-(4-methylphenyl)cyclobutyl-N-hydroxy-N-benzamide |
| Example 90 | 4-bromobenzaldehyde | 3-(4-bromophenyl)cyclobutyl-N-hydroxy-N-benzamide |
| Example 91 | 4-methoxybenzaldehyde | 3-(4-methoxyphenyl)cyclobutyl-N-hydroxy-N-acetamide |

TABLE III-continued

| | Aldehyde Precursor | Product |
|---|---|---|
| Example 92 | 4-isobutylbenzaldehyde | 4-isobutylphenyl cyclobutyl N-hydroxy-N-acetamide |
| Example 93 | pyridine-2-carboxaldehyde | 2-pyridyl cyclobutyl N-hydroxy-N-acetamide |
| Example 94 | 6-methylpyridine-2-carboxaldehyde | 6-methyl-2-pyridyl cyclobutyl N-hydroxy-N-acetamide |
| Example 95 | pyridine-3-carboxaldehyde | 3-pyridyl cyclobutyl N-hydroxy-N-propionamide (CH$_2$CH$_3$) |
| Example 96 | pyridine-4-carboxaldehyde | 4-pyridyl cyclobutyl N-hydroxy-N-(C$_6$H$_{11}$)amide |
| Example 97 | benzothiophene-2-carboxaldehyde | benzothiophen-2-yl cyclobutyl N-hydroxy-N-acetamide |
| Example 98 | benzofuran-2-carboxaldehyde | benzofuran-2-yl cyclobutyl N-hydroxy-N-acetamide |

TABLE III-continued

| | Aldehyde Precursor | Product |
|---|---|---|
| Example 99 | 2-naphthaldehyde | 2-naphthyl-cyclobutyl-N(OH)-C(O)CH₃ |
| Example 100 | 1-naphthaldehyde | 1-naphthyl-cyclobutyl-N(OH)-C(O)CH₃ |
| Example 101 | 5-butoxy-thiophene-2-carbaldehyde | 5-butoxy-thiophene-2-yl-cyclobutyl-N(OH)-C(O)C₅H₉ |
| Example 102 | 5-phenoxy-thiophene-2-carbaldehyde | 5-phenoxy-thiophene-2-yl-cyclobutyl-N(OH)-C(O)CH₃ |
| Example 103 | 5-(4-methylphenoxy)-thiophene-2-carbaldehyde | 5-(4-methylphenoxy)-thiophene-2-yl-cyclobutyl-N(OH)-C(O)C₆H₁₁ |
| Example 104 | 5-(4-methoxyphenoxy)-thiophene-2-carbaldehyde | 5-(4-methoxyphenoxy)-thiophene-2-yl-cyclobutyl-N(OH)-C(O)CHC₆H₅ |
| Example 105 | 5-(4-chlorophenoxy)-thiophene-2-carbaldehyde | 5-(4-chlorophenoxy)-thiophene-2-yl-cyclobutyl-N(OH)-C(O)C₆H₁₁ |

We claim:

1. A compound having the structure

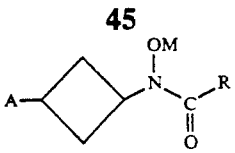

or a pharmaceutically acceptable salt thereof wherein
M represents hydrogen, a pharmaceutically acceptable cation, or a pharmaceutically acceptable metabolically cleavable group;
R is selected from the group consisting of hydrogen,
alkyl of from one to twelve carbon atoms,
cycloalkyl of from three to eight carbon atoms,
and —NR$^1$R$^2$ wherein
R$^1$ is selected from the group consisting of hydrogen,
alkyl of from one to six carbon atoms,
hydroxyalkyl of from one to six carbons atoms, and
alkoxyalkyl in which the alkoxy portion and the alkyl portion each contain, independently, from one to six carbon atoms; and
R$^2$ is selected from the group consisting of
hydrogen,
hydroxy,
alkyl of from one to six carbon atoms,
hydroxyalkyl of from one to six carbon atoms,
alkoxyalkyl in which the alkoxy portion and the alkyl portion each contain, independently, from one to six carbon atoms,
alkanoyl of from two to eight carbon atoms,
alkyl(carbocyclic aryl) in which the alkyl portion contains from one to six carbon atoms, and
optionally substituted (carbocyclic aryl);
A is selected from the group consisting of
(a) alkyl of from five to twenty carbon atoms;
(b) cycloalkyl of from three to eight carbon atoms;
(c) optionally substituted carbocyclic aryl;
(d) optionally substituted (carbocyclic aryl)cycloalkyl in which the cycloalkyl portion may contain from three to eight carbon atoms;
(e) optionally substituted (carbocyclic aryl)alkyl in which the alkyl portion may contain from one to six carbon atoms;
(f) optionally substituted carbocyclic aryloxyalkyl in which the alkyl portion contains from one to six carbon atoms;
(g) optionally substituted (carbocyclic aryl)alkoxyalkyl in which the alkoxyl and alkyl portions may independently contain from one to six carbon atoms;
(h) optionally substituted carbocyclic arylthioalkyl in which the alkyl portion may contain from one to six carbon atoms;
wherein the optional substituents on the carbocyclic aryl groups are selected from the group consisting of
alkyl of from one to six carbon atoms,
haloalkyl of from one to six carbon atoms,
alkoxy of from one to twelve carbon atoms,
alkoxyalkoxyl in which the two alkoxy portions may each independently contain from one to six carbon atoms,
phenyl, optionally substituted with
alkyl of from one to six carbon atoms,
haloalkyl of from one to six carbon atoms,
alkoxy of from one to six carbon atoms,
hydroxy, or
halogen,
phenoxy, optionally substituted with
alkyl of from one to six carbon atoms,
haloalkyl of from one to six carbon atoms,
alkoxy of from one to six carbon atoms,
halogen,
phenylthio, optionally substituted with
alkyl of from one to six carbon atoms,
haloalkyl of from one to six carbon atoms,
alkoxy of from one to six carbon atoms,
halogen,
2-, 3-, or 4-pyridyl, optionally substituted with
alkyl of from one to six carbon atoms,
haloalkyl of from one to six carbon atoms,
alkoxy of from one to six carbon atoms,
halogen,
2-, 3-, or 4-pyridyloxy, optionally substituted with
alkyl of from one to six carbon atoms,
haloalkyl of from one to six carbon atoms,
alkoxy of from one to six carbon atoms,
halogen,
(i) 2- or 3-furyl, optionally substituted with
alkyl of from one to six carbon atoms;
haloalkyl of from one to six carbon atoms;
alkoxy of from one to six carbon atoms;
halogen,
phenyl, optionally substituted with
alkyl of from one to six carbon atoms,
haloalkyl of from one to six carbon atoms,
alkoxy of from one to six carbon atoms,
halogen,
phenoxy, optionally substituted with
alkyl of from one to six carbon atoms,
haloalkyl of from one to six carbon atoms,
alkoxy of from one to six carbon atoms,
halogen,
phenylthio, optionally substituted with
alkyl of from one to six carbon atoms,
haloalkyl of from one to six carbon atoms,
alkoxy of from one to six carbon atoms,
halogen,
2-, 3,-, or 4-pyridyl, optionally substituted with
alkyl of from one to six carbon atoms,
haloalkyl of from one to six carbon atoms,
alkoxy of from one to six carbon atoms,
halogen,
2-, 3-, or 4-pyridyloxy, optionally substituted with
alkyl of from one to six carbon atoms,
haloalkyl of from one to six carbon atoms,
alkoxy of from one to six carbon atoms,
halogen,
(j) benzo[b]furyl, optionally substituted with
alkyl of from one to six carbon atoms,
haloalkyl of from one to six carbon atoms,
alkoxyl of from one to six carbon atoms, or
halogen;
(k) 2- or 3-thienyl, optionally substituted with
alkyl of from one to six carbon atoms;
haloalkyl of from one to six carbon atoms;
alkoxy of from one to six carbon atoms;
halogen,
phenyl, optionally substituted with
alkyl of from one to six carbon atoms,
haloalkyl of from one to six carbon atoms,
alkoxy of from one to six carbon atoms,
halogen, phenoxy, optionally substituted with
  alkyl of from one to six carbon atoms,
  haloalkyl of from one to six carbon atoms,
  alkoxy of from one to six carbon atoms,
  halogen,
phenylthio, optionally substituted with
  alkyl of from one to six carbon atoms,
  haloalkyl of from one to six carbon atoms,
  alkoxy of from one to six carbon atoms,
  halogen,
2-, 3-, or 4-pyridyl, optionally substituted with
  alkyl of from one to six carbon atoms,
  haloalkyl of from one to six carbon atoms,
  alkoxy of from one to six carbon atoms,
  halogen,
2-, 3-, or 4-pyridyloxy, optionally substituted with
  alkyl of from one to six carbon atoms,
  haloalkyl of from one to six carbon atoms,
  alkoxy of from one to six carbon atoms, or
  halogen; and
(1) 2- or 3-benzo[b]thienyl, optionally substituted with
  alkyl of from one to six carbon atoms,
  haloalkyl of from one to six carbon atoms;
  alkoxyl of from one to six carbon atoms, or
  halogen.

2. A compound as defined by claim 1 or a pharmaceutically acceptable salt thereof wherein M and R are as defined therein and A is selected from the group consisting of
(a) alkyl of from five to twenty carbon atoms;
(b) cycloalkyl of from three to eight carbon atoms;
(c) optionally substituted carbocyclic aryl;
wherein the optional substituents on the carbocyclic aryl groups are selected from the group consisting of
  alkyl of from one to six carbon atoms,
  haloalkyl of from one to six carbon atoms,
  alkoxy of from one to twelve carbon atoms,
  phenyl, optionally substituted with
    alkyl of from one to six carbon atoms,
    alkoxy of from one to six carbon atoms,
    halogen,
  phenoxy, optionally substituted with
    alkyl of from one to six carbon atoms,
    haloalkyl of from one to six carbon atoms,
    alkoxy of from one to six carbon atoms,
    halogen,
  phenylthio, optionally substituted with
    alkyl of from one to six carbon atoms,
    haloalkyl of from one to six carbon atoms,
    alkoxy of from one to six carbon atoms,
    halogen, 3. A compound as defined by claim 1 or a pharmaceutically acceptable salt thereof wherein M and R are as defined therein and A is selected from the group consisting of
(a) alkyl of from five to twenty carbon atoms;
(b) cycloalkyl of from three to eight carbon atoms;
(c) optionally substituted carbocyclic aryl;
wherein the optional substituents on the carbocyclic aryl groups are selected from
  2-, 3-, or 4-pyridyl, optionally substituted with
    alkyl of from one to six carbon atoms,
    haloalkyl of from one to six carbon atoms,
    alkoxy of from one to six carbon atoms,
    hydroxy or
    halogen,
  2-, 3-, or 4-pyridyloxy, optionally substituted with
    alkyl of from one to six carbon atoms,
    haloalkyl of from one to six carbon atoms,
    alkoxy of from one to six carbon atoms,
    hydroxy or
    halogen.

4. A compound as defined by claim 1 or a pharmaceutically acceptable salt thereof wherein M and R are as defined therein and A is selected from the group consisting of
  2- or 3-furyl, optionally substituted with
    alkyl of from one to six carbon atoms;
    haloalkyl of from one to six carbon atoms;
    alkoxy of from one to six carbon atoms;
    halogen,
  phenyl, optionally substituted with
    alkyl of from one to six carbon atoms,
    haloalkyl of from one to six carbon atoms,
    alkoxy of from one to six carbon atoms,
    halogen,
  phenoxy, optionally substituted with
    alkyl of from one to six carbon atoms,
    haloalkyl of from one to six carbon atoms,
    alkoxy of from one to six carbon atoms,
    halogen,
  phenylthio, optionally substituted with
    alkyl of from one to six carbon atoms,
    haloalkyl of from one to six carbon atoms,
    alkoxy of from one to six carbon atoms,
    halogen,
  2- 3,- or 4-pyridyl, optionally substituted with
    alkyl of from one to six carbon atoms,
    haloalkyl of from one to six carbon atoms,
    alkoxy of from one to six carbon atoms,
    halogen,
  2-, 3-, or 4-pyridyloxy, optionally substituted with
    alkyl of from one to six carbon atoms,
    haloalkyl of from one to six carbon atoms,
    alkoxy of from one to six carbon atoms,
    halogen,
  benzo[b]furyl, optionally substituted with
    alkyl of from one to six carbon atoms,
    haloalkyl of from one to six carbon atoms,
    alkoxyl of from one to six carbon atoms, or
    halogen;
  2-, or 3-thienyl, optionally substituted with
    alkyl of from one to six carbon atoms;
    haloalkyl of from one to six carbon atoms;
    alkoxy of from one to six carbon atoms;
    halogen,
  phenyl, optionally substituted with
    alkyl of from one to six carbon atoms,
    haloalkyl of from one to six carbon atoms,
    alkoxy of from one to six carbon atoms,
    halogen,
  phenoxy, optionally substituted with
    alkyl of from one to six carbon atoms,
    haloalkyl of from one to six carbon atoms,
    alkoxy of from one to six carbon atoms,
    halogen,
  phenylthio, optionally substituted with
    alkyl of from one to six carbon atoms,
    haloalkyl of from one to six carbon atoms,
    alkoxy of from one to six carbon atoms,
    halogen,
  2-, 3,- or 4-pyridyl, optionally substituted with
    alkyl of from one to six carbon atoms, haloalkyl of from one to six carbon atoms,
alkoxy of from one to six carbon atoms,
halogen,
2-, 3-, or 4-pyridyloxy, optionally substituted with
  alkyl of from one to six carbon atoms,
  haloalkyl of from one to six carbon atoms,
  alkoxy of from one to six carbon atoms, or
  halogen; and
2- or 3-benzo[b]thienyl, optionally substituted with
  alkyl of from one to six carbon atoms,
  haloalkyl of from one to six carbon atoms;
  alkoxyl of from one to six carbon atoms, or
  halogen.

5. A compound as defined by claim 1 having the structure

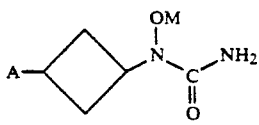

or a pharmaceutically acceptable salt thereof wherein
M represents hydrogen or a pharmaceutically acceptable cation, or a pharmaceutically acceptable metabolically cleavable group;
A is selected from the group consisting of
  (a) alkyl of from five to twenty carbon atoms;
  (b) cycloalkyl of from three to eight carbon atoms;
  (c) optionally substituted carbocyclic aryl;
  (d) optionally substituted (carbocyclic aryl)cycloalkyl in which the cycloalkyl portion may contain from three to eight carbon atoms;
  (e) optionally substituted (carbocyclic aryl)alkyl in which the alkyl portion may contain from one to six carbon atoms;
  (f) optionally substituted carbocyclic aryloxyalkyl in which the alkyl portion contains from one to six carbon atoms;
  (g) optionally substituted (carbocyclic aryl)alkoxyalkyl in which the alkoxyl and alkyl portions may independently contain from one to six carbon atoms;
  (h) optionally substituted carbocyclic arylthioalkyl in which the alkyl portion may contain from one to six carbon atoms;
wherein the optional substituents on the carbocyclic aryl groups are selected from the group consisting of
  alkyl of from one to six carbon atoms,
  haloalkyl of from one to six carbon atoms,
  hydroxyalkyl of from one to six carbon atoms,
  alkoxy of from one to twelve carbon atoms,
  alkoxyalkoxyl in which the two alkoxy portions may each independently contain from one to six carbon atoms,
  alkylthio of from one to six carbon atoms,
  phenyl, optionally substituted with
    alkyl of from one to six carbon atoms,
    haloalkyl of from one to six carbon atoms,
    alkoxy of from one to six carbon atoms,
    halogen,
  phenoxy, optionally substituted with
    alkyl of from one to six carbon atoms,
    haloalkyl of from one to six carbon atoms,
    alkoxy of from one to six carbon atoms,
    halogen, and
  phenylthio, optionally substituted with
    alkyl of from one to six carbon atoms,
    haloalkyl of from one to six carbon atoms,
    alkoxy of from one to six carbon atoms, and
    halogen.

6. A compound as defined by claim 1 having the structure

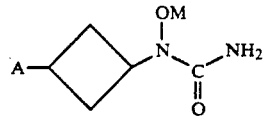

or a pharmaceutically acceptable salt thereof wherein
M represents hydrogen or a pharmaceutically acceptable cation, or a pharmaceutically acceptable metabolically cleavable group;
A is selected from the group consisting of
  (a) alkyl of from five to twenty carbon atoms;
  (b) cycloalkyl of from three to eight carbon atoms;
  (c) optionally substituted carbocyclic aryl;
  (d) optionally substituted (carbocyclic aryl)cycloalkyl in which the cycloalkyl portion may contain from three to eight carbon atoms;
  (e) optionally substituted (carbocyclic aryl)alkyl in which the alkyl portion may contain from one to six carbon atoms;
  (f) optionally substituted carbocyclic aryloxyalkyl in which the alkyl portion contains from one to six carbon atoms;
  (g) optionally substituted (carbocyclic aryl)alkoxyalkyl in which the alkoxyl and alkyl portions may independently contain from one to six carbon atoms;
  (h) optionally substituted carbocyclic arylthioalkyl in which the alkyl portion may contain from one to six carbon atoms;
wherein the optional substituents on the carbocyclic aryl groups are selected from the group consisting of
  2-, 3-, or 4-pyridyl, optionally substituted with
    alkyl of from one to six carbon atoms,
    haloalkyl of from one to six carbon atoms,
    alkoxy of from one to six carbon atoms,
    halogen, and
  2-, 3-, or 4-pyridyloxy, optionally substituted with
    alkyl of from one to six carbon atoms,
    haloalkyl of from one to six carbon atoms,
    alkoxy of from one to six carbon atoms, and
    halogen.

7. A compound as defined by claim 1 having the structure

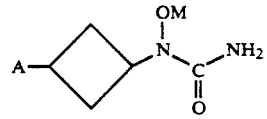

or a pharmaceutically acceptable salt thereof wherein
M represents hydrogen or a pharmaceutically acceptable cation, or a pharmaceutically acceptable metabolically cleavable group;
A is selected from the group consisting of
  2- or 3-furyl, optionally substituted with
    alkyl of from one to six carbon atoms;
  phenyl, optionally substituted with
    alkyl of from one to six carbon atoms, haloalkyl of from one to six carbon atoms,
alkoxy of from one to six carbon atoms,
halogen,
phenoxy, optionally substituted with
  alkyl of from one to six carbon atoms,
  haloalkyl of from one to six carbon atoms,
  alkoxy of from one to six carbon atoms,
  halogen,
phenylthio, optionally substituted with
  alkyl of from one to six carbon atoms,
  haloalkyl of from one to six carbon atoms,
  alkoxy of from one to six carbon atoms,
  halogen,
2-, 3-, or 4-pyridyl, optionally substituted with
  alkyl of from one to six carbon atoms,
  haloalkyl of from one to six carbon atoms,
  alkoxy of from one to six carbon atoms,
  halogen,
2-, 3-, or 4-pyridyloxy, optionally substituted with
  alkyl of from one to six carbon atoms,
  haloalkyl of from one to six carbon atoms,
  alkoxy of from one to six carbon atoms,
  halogen, and
benzo[b]furyl, optionally substituted with
  alkyl of from one to six carbon atoms,
  haloalkyl of from one to six carbon atoms,
  alkoxyl of from one to six carbon atoms, or
  halogen.

8. A compound as defined by claim 1 having the structure

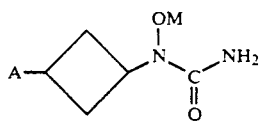

or a pharmaceutically acceptable salt thereof wherein
M represents hydrogen or a pharmaceutically acceptable cation, or a pharmaceutically acceptable metabolically cleavable group;
A is selected from the group consisting of
2- or 3-thienyl, optionally substituted with
  alkyl of from one to six carbon atoms;
phenyl, optionally substituted with
  alkyl of from one to six carbon atoms,
  haloalkyl of from one to six carbon atoms,
  alkoxy of from one to six carbon atoms,
  halogen,
phenoxy, optionally substituted with
  alkyl of from one to six carbon atoms,
  haloalkyl of from one to six carbon atoms,
  alkoxy of from one to six carbon atoms,
  halogen,
phenylthio, optionally substituted with
  alkyl of from one to six carbon atoms,
  haloalkyl of from one to six carbon atoms,
  alkoxy of from one to six carbon atoms,
  halogen,
2-, 3-, or 4-pyridyl, optionally substituted with
  alkyl of from one to six carbon atoms,
  haloalkyl of from one to six carbon atoms,
  alkoxy of from one to six carbon atoms,
  halogen,
2-, 3-, or 4-pyridyloxy, optionally substituted with
  alkyl of from one to six carbon atoms,
  haloalkyl of from one to six carbon atoms,
  alkoxy of from one to six carbon atoms, or
  halogen; and
2- or 3-benzo[b]thienyl, optionally subtituted with
  alkyl of from one to six carbon atoms,
  haloalkyl of from one to six carbon atoms;
  alkoxyl of from one to six carbon atoms, or
  halogen.

9. A compound as defined by claim 1 selected from the group consisting of
N-[3-(3-(4-fluorophenoxy)phenyl)-cyclobutyl]-N-hydroxyurea
N-[3-phenylcyclobutyl]-N-hydroxyurea         -yl)-cyclobutyl]-N-hydroxyurea
N-[3-(5-(4-fluorophenoxy)thien-2
N-[3-(6-methoxy-2-naphthyl)-cyclobutyl]-N-hydroxyurea
N-[3-(4-biphenyl)-cyclobutyl]-N-hydroxyurea
N-[3-(3-methoxyphenyl)-cyclobutyl]-N-hydroxyacetamide.

10. A pharmaceutical composition for inhibiting the biosynthesis of leukotrienes comprising a therapeutically effective amount of a compound as defined by claim 1 in combination with a pharmaceutically acceptable carrier.

11. A method of inhibiting the biosynthesis of leukotrienes comprising adminstering to a mammal in need of such treatment a therapeutically effective amount of a compound as defined by claim 1.

* * * * *